United States Patent
Metala et al.

(10) Patent No.: US 8,438,929 B2
(45) Date of Patent: May 14, 2013

(54) PHASED ARRAY ULTRASONIC INSPECTION SYSTEM FOR TURBINE AND GENERATOR ROTOR BORE

(75) Inventors: Michael J. Metala, Murrysville, PA (US); Waheed A. Abbasi, Murrysville, PA (US)

(73) Assignee: Siemens Energy, Inc., Orlando, FL (US)

( * ) Notice: Subject to any disclaimer, the term of this patent is extended or adjusted under 35 U.S.C. 154(b) by 327 days.

(21) Appl. No.: 12/874,289

(22) Filed: Sep. 2, 2010

(65) Prior Publication Data

US 2012/0055255 A1    Mar. 8, 2012

(51) Int. Cl.
*G01M 13/00* (2006.01)

(52) U.S. Cl.
USPC .................................. 73/660; 73/593; 73/602

(58) Field of Classification Search .................... 73/660, 73/593, 602, 620, 625, 626, 628
See application file for complete search history.

(56) References Cited

U.S. PATENT DOCUMENTS

| | | | | |
|---|---|---|---|---|
| 5,189,915 A * | 3/1993 | Reinhart et al. | ................ | 73/623 |
| 6,082,198 A | 7/2000 | Sabourin et al. | | |
| 6,736,011 B2 * | 5/2004 | Zayicek et al. | ................ | 73/628 |
| 7,428,842 B2 * | 9/2008 | Fair et al. | ......................... | 73/626 |
| 7,617,733 B2 * | 11/2009 | Deemer et al. | ................... | 73/660 |
| 7,654,143 B2 * | 2/2010 | Roney et al. | ..................... | 73/620 |
| 7,690,257 B2 * | 4/2010 | Meier et al. | ..................... | 73/588 |
| 7,735,370 B2 * | 6/2010 | Burat et al. | ..................... | 73/660 |
| 7,841,237 B2 * | 11/2010 | Suzuki et al. | ................... | 73/623 |
| 8,240,042 B2 * | 8/2012 | Williams et al. | ............. | 29/889.1 |
| 2002/0088282 A1 | 7/2002 | Zayicek et al. | | |
| 2006/0283250 A1 | 12/2006 | Fair et al. | | |
| 2008/0245151 A1 * | 10/2008 | Roney et al. | ..................... | 73/628 |
| 2011/0277549 A1 * | 11/2011 | Frederick et al. | ............... | 73/627 |

FOREIGN PATENT DOCUMENTS

EP    0622629 A1    11/1994

* cited by examiner

*Primary Examiner* — J M Saint Surin

(57) ABSTRACT

A phased array ultrasonic testing system for examining discontinuities in turbine or generator rotor bores formed within turbine or generator rotors of a turbine or generator rotor assembly. The system includes a phased array ultrasonic transducer structured to be coupled to a surface of the rotor bore at a first location in order to emit an ultrasonic beam toward a second location of the rotor bore which is to be examined. The system further includes a control system with a computer and a controller for programming, emitting, and steering the ultrasonic beam via at least one, two-dimensional phased array transducer, thereby precisely and accurately inspecting the area of interest. Computer control of the beam permits the number of inspection locations and the number of different transducer wedges to be reduced providing for an efficient, timely inspection.

15 Claims, 3 Drawing Sheets

PHASED ARRAY ULTRASONIC INSPECTION SYSTEM FOR TURBINE AND GENERATOR ROTOR BORE

FIELD OF THE INVENTION

The present invention generally relates to ultrasonic, non-destructive testing, and more particularly, to a phased array ultrasonic testing system and method for inspecting and/or examining power generation equipment and other industrial equipment. In particular, the present invention relates to a phased array ultrasonic testing system and method for inspecting and/or examining turbine and generator components, such as turbine and generator rotor bores, for discontinuities.

BACKGROUND OF THE INVENTION

It is known in the art to routinely inspect steam turbines and generators used for electrical power generation to detect discontinuities. Rotor bore inspections are performed on power generating equipment, such as turbines and generators. These inspections are typically carried out using a variety of convention methods, such as ultrasonic inspection and eddy current inspection. The ultrasonic inspection is employed to inspect areas that are inside the volume of the rotor around the bore, and the eddy current inspection is employed to inspect the bore surface. Other methods, such as visual and magnetic particle examination, have been used successfully to inspect the bore, but some of these methods are only sensitive to discontinuities which intersect or are very near to the bore and then only yield a two-dimensional view of the material and any detected discontinuities.

The objective of these inspections is to determine the presence of flaws or discontinuities inside the volume of the rotor. The results obtained from the inspections are utilized to assess the condition and integrity of the component. The assessment of the component is based on the characteristics of the flaws or discontinuities, such as, for example, size, orientation and location. The greater the precision and accuracy of the inspection technique and data obtained therefrom, the more reliable is the assessment for determining the condition of the component. It is desired to identify discontinuities to preclude progression to a point where they risk the integrity of the component and potential component failure. The consequences of a sudden, catastrophic failure of such a component could be severe. However, there are instances where a large margin of safety is built into the analysis to compensate for the lack of accuracy and resolution of the inspection data. While this approach is safe, it can be inefficient in that the component actually may be able to operate safely for a period of time that extends beyond that identified by a conservative assessment.

A typical manufacturing process for turbine and generator rotors that are currently in service included a forging process that migrated impurities into the center of the forging. The impurities could be removed by drilling a hole (e.g., bore hole) through the center of the rotor. The size of the bore hole diameter generally relates to the amount and location of impurities near the center line of the rotor. A greater number of impurities resulted in a larger diameter hole being drilled. Although drilling the bore hole is a mechanism for removing most of the impurities, the bore hole can be stressed during operation of the rotor, which can lead to discontinuities in the rotor material. Additionally, other impurities or inclusions that remained outside of the bored area (volume) could grow under service-related stress and could potentially result in a failure.

Conventional ultrasonic inspection methods include applying high-frequency sound waves to the structure being tested using one or more transducers. The transducers typically include piezocrystal elements that are excited by an electrical voltage to induce the ultrasonic waves in the structure. When the ultrasound waves interact with something (e.g., a void, a crack or other defect) having a significant difference in impedance from that of the propagation medium, a portion of the ultrasound is either reflected or diffracted back to the source from which it originated. Detection and quantification of the returned ultrasound pattern is used to determine the characteristics of the reflecting medium. In this method, referred to as rotor boresonic inspection, an automated system is typically used to transport ultrasonic transducers inside the rotor bore hole by some convenient method, and the transducers direct sound, i.e., ultrasonic waves or beams, from the rotor bore surface into the rotor material and toward the rotor bore's outside diameter. The ultrasonic wave can penetrate well into the rotor material, and by collecting, processing, and observing any reflections of the wave which occur within the forging, one can get some idea of the integrity of the material.

In a rotor boresonic inspection, longitudinal ultrasound is directed in a radial direction; shear wave ultrasound is directed at angles from the bore surface clockwise and counter clockwise around the rotor and shear wave ultrasound is also directed in an axial direction along the length of the rotor.

Standard ultrasonic transducers can be used to accomplish rotor boresonic inspection. For example, a shear wave angle beam inspection uses plexiglass wedges to refract the beam to a predetermined fixed angle. If other angles are required during the inspection, the transducers are removed and the wedges changed to obtain the desired refracted angle. Transducer and wedge change out is time consuming and requires numerous wedges and transducers to sweep through several different angles of attack.

Phased array ultrasonic technology generally provides for computer-controlled excitation (e.g., amplitude and delay) of individual elements in a multi-element transducer (as opposed to single-element transducers of conventional ultrasonic inspection). The excitation of piezocomposite elements can generate a focused ultrasonic beam with the potential to modify beam parameters, such as angle, focal distance, and focal point through software. Thus, a computer-controlled beam scanning pattern can be implemented in order to direct or steer the beam to the area of interest and to search for cracks and other discontinuities in the rotor bore.

In a particular known ultrasonic testing system, the transducers are placed on the outside of the turbine or generator rotor and the phased arrays are employed to inspect from the outside of a bore to the inside of the bore. In another known system, water is introduced inside of the rotor and the transducers used to inspect and examine the turbine or generator rotor bores are immersed in the water. Further, in these known systems, each of the transducers are positioned to collect data from a beam emitted from the transducer. The beam is emitted in a single, fixed pre-set/pre-specified direction. The direction of the transducer can be changed by re-positioning the transducer in accordance with the desired direction. For example, the fixed angle wedges previously described herein can be used to re-position the transducer to emit a beam in a different direction.

There remains a need for an improved ultrasonic testing system of turbine and generator rotor bores. The capabilities of known systems have limitations. For example, known systems utilize fixed angle wedges to steer the beam and therefore, re-direction of the beam requires the transducer to be removed and re-positioned at a different location. Further, known systems can include a beam having a fixed focal point such that areas in the near field and far field of the transducer are not inspected. Thus, it is desired to provide an ultrasonic testing system that provides an array of angles to inspect an area of interest (e.g., sectorial scan) and provides the ability to change the focal depth of the transducer.

SUMMARY OF THE INVENTION

These needs and others are satisfied by the present invention, which relates to a system and method for inspecting industrial machinery, such as turbine and generator components, for example, turbine and generator rotor bores, using advanced phased array ultrasonic testing apparatus and methods.

As one aspect of the invention, a phased array ultrasonic testing system is provided for examining a rotor bore formed within a rotor of a turbine or generator rotor assembly. The rotor has an interior surface and an exterior surface. The interior surface serves as a surface of the rotor bore. The phased array ultrasonic testing system includes a phased array ultrasonic transducer structured to be coupled to the surface of the rotor bore at a first location. The phased array ultrasonic transducer emits an ultrasonic beam from the first location toward a second location of the surface of the rotor bore. A control system adapted to define a plurality of focal laws of the ultrasonic beam, controls the emission of the ultrasonic beam from the phased array ultrasonic transducer and steers and focuses the ultrasonic beam to conduct a non-destructive examination of the rotor bore.

The control system may include a computer and a controller wherein the computer is structured to program the controller which is adapted to manipulate the transducer in order to perform the examination. At least one of the phased array ultrasonic transducers may be a two-dimensional phased array transducer having a plurality of elements wherein the control system is adapted to actuate the elements in order to steer the beam in a first direction and in a second direction.

As another aspect of the invention, a method of ultrasonically examining a rotor bore formed in a rotor of a turbine or generator rotor assembly. The method includes coupling a phased array ultrasonic transducer at a first location on a surface of the rotor bore, emitting an ultrasonic beam from the phased array ultrasonic transducer at the first location toward a second location of the rotor bore which is to be examined, calculating a plurality of focal laws for the ultrasonic beam, programming a control system in accordance with the focal laws to control the emission of the ultrasonic beam from the phased array ultrasonic transducer, and steering and focusing the ultrasonic beam to a portion of the rotor bore to be examined.

The method may further include collecting ultrasonic data from the portion of the turbine or generator rotor bore and analyzing the data to detect discontinuities therein.

Performing the ultrasonic examination of the turbine or generator rotor bore may include using an ultrasonic testing technique selected from the group consisting of pulse echo, pitch catch, electronic scanning, dynamic depth focusing, sectorial scanning, and a combination thereof.

The method may further include programming a controller of the control system using a computer, including defining the focal laws for the ultrasonic beam. The programming step may comprise defining as the focal laws, focal laws selected from the group consisting of beam angle, focal distance, beam width, focal point and combinations thereof.

DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
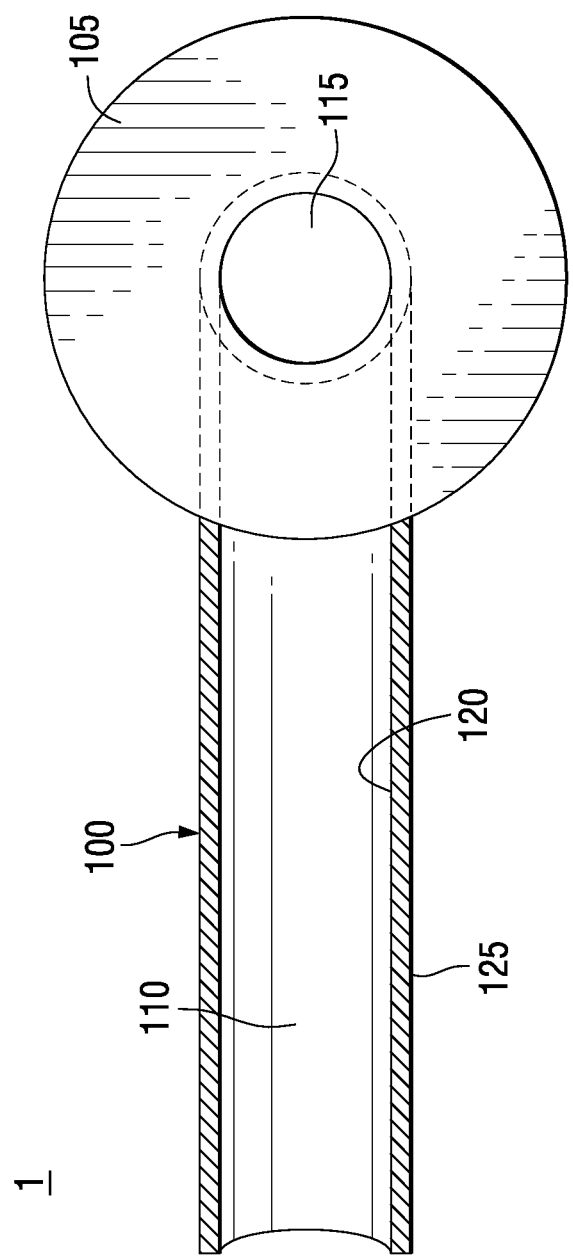
FIG. 1 is a cross-sectional view of a prior art turbine rotor assembly.

The present invention relates to an ultrasonic testing system and method for inspecting and examining various components of industrial machinery, such as, but not limited to, turbine and generator components, such as, for example, the rotor bore formed within the rotor of a turbine or generator rotor assembly. The results obtained from ultrasonic testing inspections are utilized to assess the condition of the component.

The present invention can be applied to a wide variety of industrial equipment and, in particular, to power generation equipment. However, for ease of description, the present invention will be described herein as applied to the ultrasonic inspection of power generation turbines (e.g., generators and steam turbines).

Directional phrases used herein, such as, for example, "upper," "lower," "top," "bottom," "left," "right," and derivatives thereof, relate to the orientation of the elements shown in the drawings and are not limiting upon the claims unless expressly recited therein.

As employed herein, the statement that two or more parts are "coupled" together shall mean that the parts are joined together either directly or joined through one or more intermediate parts.

As employed herein, the phrase "complex geometry" refers to an object that has a variety of different shapes and configurations, such that one portion of the object has a shape or configuration which is substantially different from another portion of the object. For example, without limitation, a compound curve is a complex geometry as used herein. A compound curve is one that changes or varies in more than one direction or dimension (e.g., includes both convex and concave portions).

The present invention employs phased array ultrasonic testing to inspect equipment employed in generating power, such as turbines and generators, and, for example, turbine and generator rotors and, more particularly, bores formed within the turbine and generator rotors. Phased array ultrasonic testing systems can include a single transducer or multiple transducers. Each of the transducers is typically manufactured as a series of individual elements that form the transducer. These individual elements can be pulsed in various sequences that allow the ultrasonic energy emitted therefrom to be shaped, angled or focused with the rotor bore. The phased array transducers are coupled to a surface of the bore (e.g., the interior surface of the rotor). The use of phased array inspection transducers from the bore surface allows multiple angle beam inspection sweeps to be performed simultaneously without the need to use numerous individual wedges to refract the sound (which is necessary in conventional boresonic inspection methods). The sweeps performed can be in a vertical direction or a horizontal direction. Further, by using additional focal laws, the transducer can be focused to provide enhanced sensitivity to flaws in the rotor material without the need to change or re-position the transducer.

The results of phased array ultrasonic testing are used to assess the condition and integrity of the component being inspected. For example, reflections from the outer edges of a discontinuity can be used to accurately predict the extent of the indication. Other phased array techniques can be used to differentiate a relevant critical flaw from a less critical porosity defect or other minor forging defect that were pre-existing in the rotor material.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting to the scope of the invention. Furthermore, the figures show, and the following discussion relating to the figures recite, a turbine rotor assembly for ease of illustration and description. However, the figures and discussion are equally applicable to a generator rotor assembly.

FIG. 1 shows a turbine rotor assembly 1 in accordance with the invention. In the example of FIG. 1, the turbine rotor assembly 1 includes a rotor 100, a disk 105, a bore 110 and a bore opening 115. The rotor 100 has an interior surface 120 and an exterior surface 125. The interior surface 120 serves as the surface of the bore 110. The disk 105 is coupled to the rotor bore 100 using any conventional means (not shown) known in the art. The bore opening 115 provides access to the bore 110.

Figure 2:
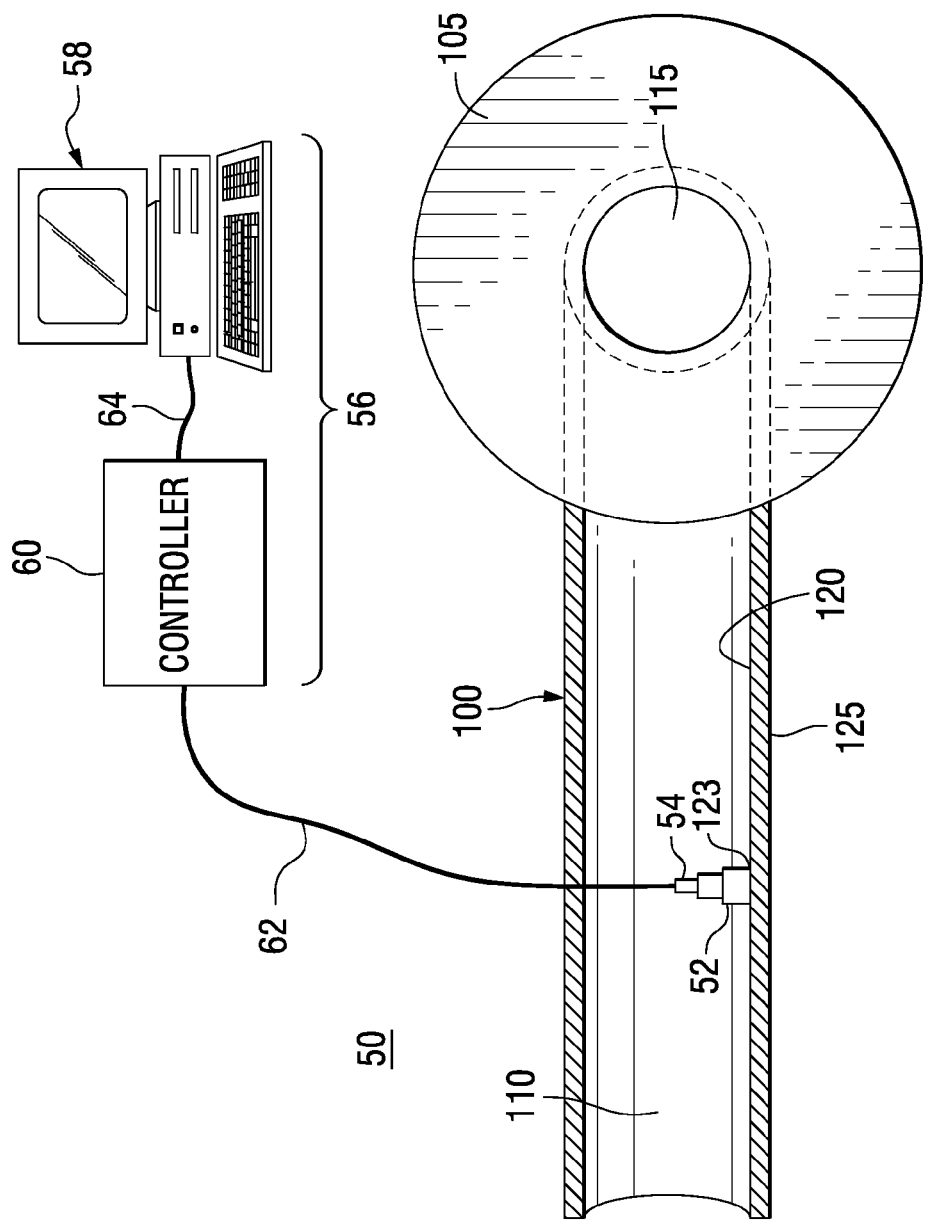
FIG. 2 is a simplified view of a phased array ultrasonic testing system as employed to inspect the turbine rotor bore in accordance with the invention.

FIG. 2 shows a phased array ultrasonic testing system 50 in accordance with one embodiment of the present invention for testing the turbine rotor assembly 1 as shown in FIG. 1. FIG. 2 includes the rotor 100, disk 105, bore 110, bore opening 115, interior rotor surface 120 and exterior rotor surface 125 as shown in FIG. 1. FIG. 2 further shows an ultrasonic transducer 54 (or probe) coupled to a wedge 52. In a further embodiment, more than one ultrasonic transducer 54 and wedge 52 combination can be employed. As previously indicated, in an embodiment, the transducer 54 and wedge 52 can be inserted through the bore opening 115 and into the bore 110 using an automated system which is conventional in the art to transport ultrasonic transducers inside the bore 110. The wedge 52 is coupled to a mounting area 123. The mounting area 123 is located on the interior rotor surface 120 which serves as the surface of the bore 110.

A beam (not shown) is emitted from the transducer 54 through the wedge 52 and then through the object being tested (e.g., bore 110). Thus, the wedge 52 serves as an optical lens-type device in order to further control (e.g., direct; steer) the beam to the desired examination area (e.g., bore 110). In this manner, the wedge 52 can partially control, for example, without limitation, the width and direction of the beam to "focus" on the area of interest. However, the steering capabilities of a particular wedge 52 are limited. Accordingly, it will be appreciated that known 1D transducers require multiple wedges in order to inspect, for example, an area of the bore 110 in FIG. 2. Selection, placement and replacement of multiple wedges on the surface of the bore (i.e., interior rotor surface 120) is a time-consuming process which greatly adds to the overall duration of the inspection. Although advancements have been made in the art to try and make wedge 52 and transducer 54 placement more efficient (see, e.g., "Self-Aligning Turbine Disc Inspection Apparatus" disclosed in U.S. Pat. No. 6,792,809), it is desirable to reduce the number of wedges 52 needed to accurately perform the inspection. The phased array ultrasonic testing system 50 and methods of the invention successfully achieve this goal by providing 2D beam steering capabilities and a control system 56 to control the beam emitted from the transducer 54.

The transducer 54 is in communication with a control system 56 via a first electrical cable 62. One end of the first electrical cable 62 is coupled to the transducer 54 and the other end of the first electrical cable 62 is coupled to the controller 60 of the control system 56. The controller 60 is coupled to the computer 58 by a second electrical cable 64. Other configurations (not shown) could be employed without departing from the scope of the invention. For example, in one embodiment, a wireless configuration (not shown) could be employed, or in another embodiment, the controller 60, for example, could be eliminated such that the transducer 54 is directly controlled by the computer 58 and software thereof.

The controller 60 can be any known or suitable phased array transducer control unit adapted to manipulate the transducer 54. More specifically, the computer 58 contains software for programming the controller 60 to manipulate the transducer 54 in accordance with a predetermined set of focal laws. Accordingly, in operation, beam parameters, such as, for example, angle, focal distance, and focal point, which collectively form the focal laws of the transducer 54, can be entered and modified using the computer 58. The beam parameters entered into the computer 58 are used to program the controller 60 to control the transducer 54 to perform an examination of the desired portion of the turbine, e.g., the turbine rotor bore, in accordance with such focal laws. It will be appreciated that any known or suitable software program can be employed to define the focal laws and all of the other necessary parameters for programming the controller 60 to conduct the desired examination. By way of a non-limiting example, a known phased array transducer controller is commercially available under the trade designation TomoScan III PA, which is available from Zetec, Canada. For example, TomoScan III PA, or a similar system, can be implemented in control system 56 in order to manage the acquisition of ultrasonic signals and to provide real-time imagining of the signals and/or offline analysis of previously acquired data. It can be used as a stand alone software package for programming the ultrasonic examination to be performed, conducting the examination and acquiring the data, and then analyzing the data for discontinuities. Alternatively, it can be used in conjunction with a wide variety of other known or suitable software packages, which may be used to separately develop the focal laws and to program the controller 60, for example.

It will be appreciated that additional systems (not shown) could be employed in combination with the phase array transducer control unit 60 of the invention. For example, without limitation, a motion control unit (not shown) may be used to control a delivery mechanism for automatically positioning and installing the transducers. As indicated previously, a delivery mechanism can be employed to deliver the transducers through the bore opening 115 and into the bore 110. In general, the delivery mechanism provides a mechanism, normally hydraulic or pneumatic, to properly position the transducer 54 within the bore 110 and a means by which the transducer 54 is held against the interior rotor surface 120.

Further, the ultrasonic data can be collected from the portion of the turbine rotor bore and the data can be analyzed to detect discontinuities therein. The analysis of the data can be performed using various techniques known in the art. For example, a software program can be employed to perform the analysis. In one embodiment, software as described in United States Patent Application Publication No. 2009/0307628, which is incorporate herein by reference, can be employed.

As previously discussed, known rotor bore ultrasonic testing techniques have generally been limited to linear or one-dimensional (1D) transducers and methods of the type described, for example, in U.S. Pat. No. 6,736,011. The transducer 54 and phased array ultrasonic testing system 50 of the present invention provide for two-dimensional (2D) inspection. To further illustrate this improved aspect of the invention, with continued reference to FIG. 2, a non-limiting EXAMPLE comparing known ultrasonic transducers and testing methods and the exemplary system 50 and method will now be provided. The following EXAMPLE is merely provided for illustrative purposes and is in no way limiting upon the scope of the present invention.

EXAMPLE

For this example, an area of the bore 110 of rotor 100 having a width of about 3 inches (7.62 centimeters) is to be examined. To inspect this area using known ultrasonic testing techniques could require about six different wedges (not shown), whereas the same area can be inspected using a single wedge 52 in accordance with the exemplary embodiment of the phased array ultrasonic testing system 50 as shown in FIG. 2. Known 1D techniques are limited in their ability to steer the beam over a relatively large area and therefore, multiple wedges are required. Specifically, as previously discussed, one-dimensional transducers can only steer in one direction which makes it difficult to control the beam as desired when the wedge and transducer are mounted on a curved surface that is not completely flat. The various transducer mounting surfaces on the interior surface of the turbine rotor bore (which is typically a cylindrical body) are curved surfaces and are not flat. Therefore, the aforementioned plurality (e.g., six) of different wedges would be required to accommodate the geometry of the bore 110 by diverging, converging or otherwise focusing, for example, the beam to the desired examination area.

Conversely, transducer 54 of the invention is programmable and controllable (e.g., can be focused) in two dimensions. Focusing the transducer 54 through the exemplary control system 56 and, in particular, by programming the controller 60 with the desired focal laws (rather than by interchanging a plurality of different wedges to achieve a similar result), substantially streamlines the inspection process. The exemplary system 50 and method are expected to substantially reduce the duration of a rotor bore inspection in comparison to the duration for a conventional system and method. Specifically, it is anticipated that the system 50 could potentially reduce inspection time to about one 12-hour period which would result in a turbine down time of potentially as little as one day, rather than about three days which is typical with conventional inspection methods. It is also expected that the number of wedges (e.g., wedge 52) required for a typical rotor bore inspection will be reduced by between about 50%-80%, or more. This is evidenced in the foregoing EXAMPLE which demonstrates a present reduction in the number of wedges of over 80% from six wedges to a single wedge 52.

In regards to this EXAMPLE, in another embodiment of the present invention, a plurality, such as, but not limited to, two, phased array transducers can be used. The additional transducer(s) contribute to optimizing the scanning time.

Figure 3:
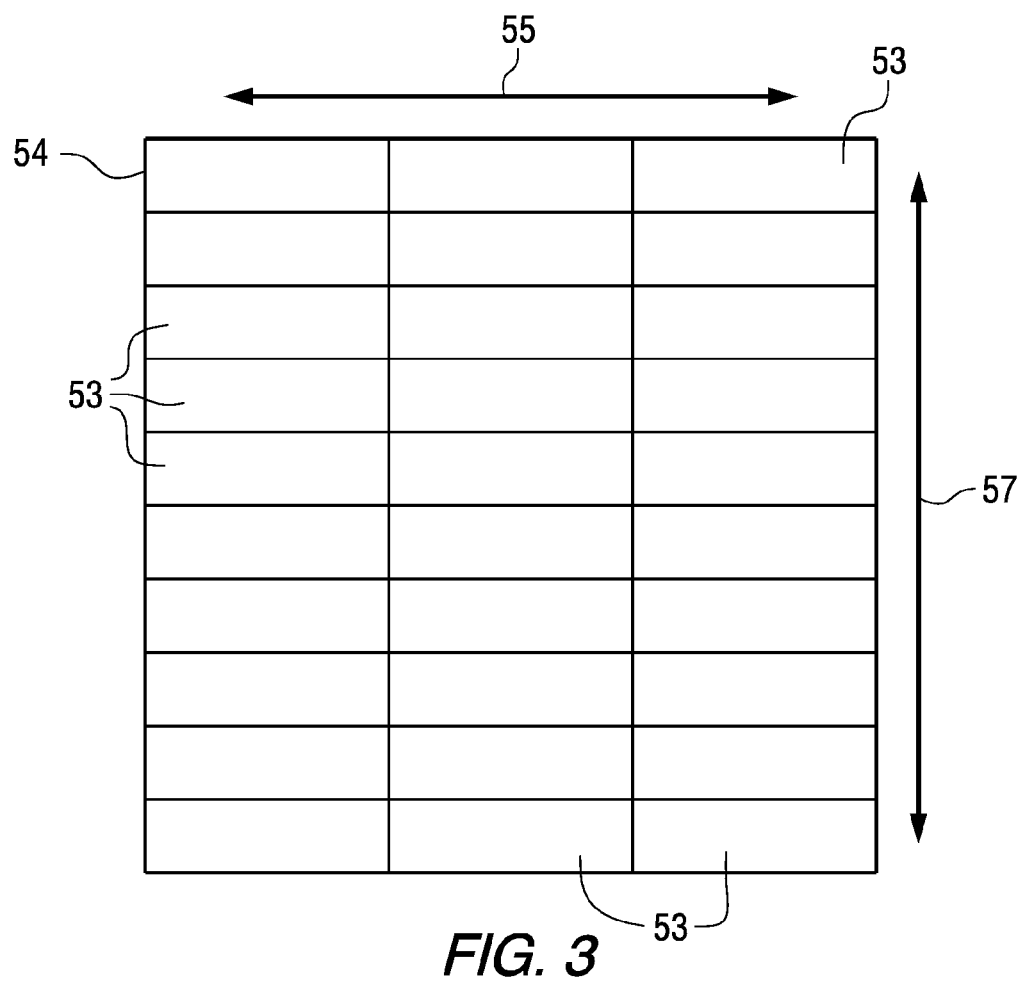
FIG. 3 is a simplified, bottom elevational view of the two-dimensional phased array transducer and the elements thereof.

FIG. 3 is a simplified view of the bottom of an exemplary transducer 54 (as shown in FIG. 2) which, as previously discussed, is a 2D phased array transducer. As shown, the exemplary 2D transducer 54 includes individual elements 53. In FIG. 3, there are thirty individual elements 53 which are disposed in a 3×10 array. Each individual element 53 essentially performs as a separate transducer to enable the ultrasonic beam emitted from transducer 54 (as shown in FIG. 2) to be steered in two directions, left to right (from the perspective of FIG. 3) as indicated by arrow 55, and up and down (with respect to FIG. 3) as indicated by arrow 57. Accordingly, as discussed hereinbefore, a single transducer 54 can be steered and focused efficiently such that it can effectively perform a comparable inspection using a reduced number of wedges, as compared to 1D designs. It will be appreciated that the present invention is not limited to employing a particular 2D phased array transducer. Any known or suitable 2D phased array transducer having any suitable number of elements can be employed with the exemplary system 50 (as shown in FIG. 2). A 2D phased array transducer of the type illustrated in FIG. 3 is commercially available, for example, without limitation, from Imasonic S.A. which has a place of business in Besancon, France. Generally, phased array transducers are custom made in accordance with the requirements of the application in which they will be used.

It will also be appreciated that, as will be described herein, the exemplary phased array ultrasonic testing system 50 (as shown in FIG. 2) and methods can also be advantageously employed to improve the performance (e.g., without limitation, steering and focusing capabilities) of 1D phased array transducers. The system 50 (as shown in FIG. 2) may also be used to collect data using conventional (e.g., non-phased array transducers) sensors (e.g., measurement sensors; thermal sensors; optical sensors) in order to profile turbine components of unknown geometry for subsequent ultrasonic examination thereof. For example, phased array transducers or non-phased array transducers can be employed to generate data from the inside volume of the bore and the bore data can be used to determine the geometry of the rotor.

It will still further be appreciated that in certain embodiments of the invention, the wedge 52 may be integral to the transducer 54 rather than being a separate component to which the transducer 54 is attached. For example, the transducer 54 may be permanently attached to the wedge 52 at a desired angle.

Further, it will be appreciated that various types or methods of ultrasonic inspection techniques can be employed, such as, but not limited to, pulse echo techniques. Generally, for pulse echo techniques, two or more 2D phased array transducers are positioned essentially adjacent one another. A beam is then emitted from each transducer such that when a defect or discontinuity is encountered, the beam from each transducer bounces back to the transducer from which it was emitted as an echo. The echo is then analyzed using the control system 56 (as shown in FIG. 2).

The foregoing pulse echo technique is merely one example of the many methods and techniques that can be employed, using the present invention to inspect the turbine rotor bore. For example, a wide variety of other known or suitable beam focusing and scanning methods, such as, for example, electronic scanning, dynamic focusing, and/or sectorial scanning (often referred to as azimuthal or angular scanning) can also be employed. Each of these methods are described in detail in

*Introduction to Phased Array Ultrasonic Technology Applications*, by Dr. Michael D. C. Moles et al., R/D Tech Inc., 2004.

As previously discussed, and shown in FIG. 2, the phased array ultrasonic-testing system 50 accomplishes the aforementioned advanced ultrasonic testing techniques through the computer-controlled manipulation of the transducer 54.

The phased array ultrasonic inspection performed in accordance with the present invention, allows for a higher resolution imaging of any flaws and discontinuities inside the volume of the rotor. It also allows for observation (interrogation) of the same flaws and discontinuities from various incident angles (sectorial scanning) which can provide for an improved interpretation of the location and size of the flaws and discontinuities as compared to the interpretation provided by conventional ultrasonic inspections.

When a company, such as, for example, Siemens Energy, Inc., examines its own turbine or generator components, parameters regarding the geometry of, for example, the turbine or generator rotor bores are known and can merely often be entered into the software when programming the focal laws. For example, engineering drawings or computer models of the components are typically available and can be imported into the software. However, the geometry is not always known, such as, for example, when inspecting turbine and generator components manufactured by another company. In such cases, the geometry of the object to be tested first can be modeled or profiled using known techniques and methods.

Accordingly, the present invention provides a system and methods to more efficiently inspect a wide variety of industrial components of known and unknown, complex and simple geometries.

The phased array ultrasonic testing system and method of the present invention provides for an accurate, precise and reliable inspection of industrial machinery, such as, for example, a turbine or generator rotor bore to detect discontinuities and flaws inside the volume of the rotor and to assess the condition and integrity of the component, e.g., turbine or generator rotor, and determine the life assessment of the component, which can be conducted in a reduced time period as compared to conventional rotor bore inspection techniques.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. A phased array ultrasonic testing system for examining a hollow rotor bore formed within a rotor of a turbine or generator rotor assembly, the rotor having an interior surface and an exterior surface, the interior surface serves as a surface of the rotor bore, the phased array ultrasonic testing system comprising: a phased array ultrasonic transducer structured to be coupled directly to the interior surface of the hollow rotor bore at a first location, the phased array ultrasonic transducer emits an ultrasonic beam from the first location toward a second location of the interior surface of the rotor bore; and a control system configured to define a plurality of focal laws of the ultrasonic beam, control the emission of the ultrasonic beam from the phased array ultrasonic transducer and steer and focus the ultrasonic beam to conduct a non-destructive examination of the hollow rotor bore, wherein the ultrasonic testing system includes a wedge disposed between the interior surface of the rotor bore and the phased array ultrasonic transducer, the wedge structured to couple the phased array ultrasonic transducer to the surface of the hollow rotor bore and to focus the ultrasonic beam on a portion of the interior rotor bore being examined.

2. The phased array ultrasonic testing system of claim 1 wherein the control system comprises a computer and a controller; and wherein the computer is structured to program the controller which is configured to manipulate the phased array ultrasonic transducer in order to perform the non-destructive examination.

3. The phased array ultrasonic testing system of claim 1 wherein the phased array ultrasonic transducer comprises a two-dimensional phased array transducer having a plurality of elements; wherein the two-dimensional phased array transducer is mounted in a stationary position on the interior surface of the rotor bore; and wherein the control system is configured to actuate the elements in order to steer the beam in a first direction and in a second direction.

4. The phased array ultrasonic testing system of claim 1 wherein the interior surface of the hollow rotor bore is a curved surface.

5. The phased array ultrasonic testing system of claim 1 wherein a plurality of phased array ultrasonic transducers are coupled to the interior surface of the rotor bore.

6. The phased array ultrasonic testing system of claim 1 wherein the phased array ultrasonic transducer comprises a plurality of elements.

7. A method of ultrasonically examining a hollow rotor bore formed within a rotor of a turbine or generator rotor assembly, the method comprising: coupling a phased array ultrasonic transducer at a first location on an interior surface of the rotor bore, emitting an ultrasonic beam from the phased array ultrasonic transducer at the first interior location toward a second location of the interior surface of the hollow rotor bore which is to be examined, calculating a plurality of focal laws for the ultrasonic beam; programming a control system in accordance with the focal laws to control the emission of the ultrasonic beam from the phased array ultrasonic transducer; and steering and focusing the ultrasonic beam to a second interior portion of the rotor bore to be examined.

8. The method of claim 7 further comprising collecting ultrasonic data from the hollow rotor bore and analyzing the data to detect one or more discontinuities therein.

9. The method of claim 7 further comprising performing the ultrasonic examination of the hollow rotor bore using an ultrasonic testing technique selected from the group consisting of pulse echo, pitch catch, electronic scanning, dynamic depth focusing, sectorial scanning, and a combination of thereof.

10. The method of claim 7 further comprising programming a controller of the control system using a computer, wherein the programming includes defining the focal laws for the ultrasonic beam.

11. The method of claim 7 further comprising the focal laws selected from the group consisting of beam angle, focal distance, beam width, focal point and combinations thereof.

12. The method of claim 7 further comprising the phased array ultrasonic transducer comprising a two-dimensional (2D) phased array transducer having a plurality of elements.

13. The method of claim 7 wherein the interior surface of the hollow rotor bore is a curved surface.

14. The method of claim 7 wherein said method is employed to determine interior geometry of the hollow rotor.

15. The method of claim 7 wherein non-phased array transducers are used to determine interior geometry of the hollow rotor.

\* \* \* \* \*